United States Patent [19]
Mertz et al.

[11] 3,980,434
[45] Sept. 14, 1976

[54] METHOD FOR DETERMINING FURAZOLIDONE IN ANIMAL TISSUE

[75] Inventors: James L. Mertz, Norwich; Joanne Olivard, Honey Grove; James P. Heotis, Norwich, all of N.Y.

[73] Assignee: Morton-Norwich Products, Inc., Norwich, N.Y.

[22] Filed: July 30, 1975

[21] Appl. No.: 600,385

[52] U.S. Cl. .......................... 23/230 B; 260/240 A; 210/31 C
[51] Int. Cl.$^2$ .................. G01N 33/16; G01N 21/00
[58] Field of Search ............... 23/230 B; 260/240 A; 210/31 C

[56] References Cited
UNITED STATES PATENTS

| | | | |
|---|---|---|---|
| 2,927,110 | 3/1960 | Gever | 260/240 A |
| 3,832,134 | 8/1974 | Sohn | 23/230 B |

OTHER PUBLICATIONS

Chemical Abstracts, 80:112711r (1974).
Chemical Abstracts, 75:117188g (1971).
Chemical Abstracts, 79:9975k (1973).

*Primary Examiner*—Morris O. Wolk
*Assistant Examiner*—Sidney Marantz
*Attorney, Agent, or Firm*—Anthony J. Franze

[57] ABSTRACT

A method for the determination of minute amounts of furazolidone in animal tissue which consists in solvent extracting furazolidone therefrom and its conversion from an ultraviolet absorbing substance to a fluorescent one by exposure to pyridine followed by irradiation with ultraviolet light thereby permitting measurement of furazolidone by fluorescence intensity.

1 Claim, No Drawings

METHOD FOR DETERMINING FURAZOLIDONE IN ANIMAL TISSUE

This invention is concerned with the provision of a method for determining minute amounts of furazolidone in animal tissue.

Furazolidone has achieved widespread use as a feed additive in the ration supplied to chickens, swine, turkeys and calves for the purpose of combatting disease and encouraging growth. A concern of paramount importance is how much, if any, furazolidone remains in the edible tissue of such animals at the time it is made available for human consumption. Until now it has not been possible to ascertain with facility via known methods for determining furazolidone minute levels of it in animal tissue with any degree of confidence.

The method of the instant invention overcomes the deficiencies of past methods and enables such determination. The method of this invention consists in the application of thin layer chromatography to the determination of furazolidone in chicken, swine, bovine and turkey tissue. It is briefly described as follows:

Tissue is quick-frozen and stored in a deep freeze chamber until required for analysis. A weighed portion of the tissue is homogenized in cold 0.25 N HCl containing NaCl. Fatty tissue, including chicken skin/fat, turkey skin/fat, swine muscle, swine fat or bovine fat is extracted with hexane. Furazolidone is recovered from the aqueous homogenate by extraction with dichloroethane (DCE) which is then evaporated to dryness. The residue is dissolved in tetrachloroethylene (TCE), furazolidone is partitioned into 0.01 N HCl, extracted with cyclohexane/benzene, and then extracted into DCE which is evaporated to dryness. The residue is then dissolved in acetone and spotted on a TLC plate by means of a TLC spotter. Furazolidone is separated from tissue constituents using programmed multiple development (PMD) thin layer chromatography. The plate is sprayed with pyridine to produce a furazolidone-pyridine complex and immediately irradiated with a high intensity, long wave ultraviolet lamp, converting the complex in situ into a highly fluorescent species which is measured with a fluorodensitometer coupled with a computing integrator. Furazolidone can be detected at a level of 2 parts per billion.

The method is described with greater particularity by the following schema showing its application to fat and non-fat tissue samples with explanatory remarks appended for each step set forth therein:

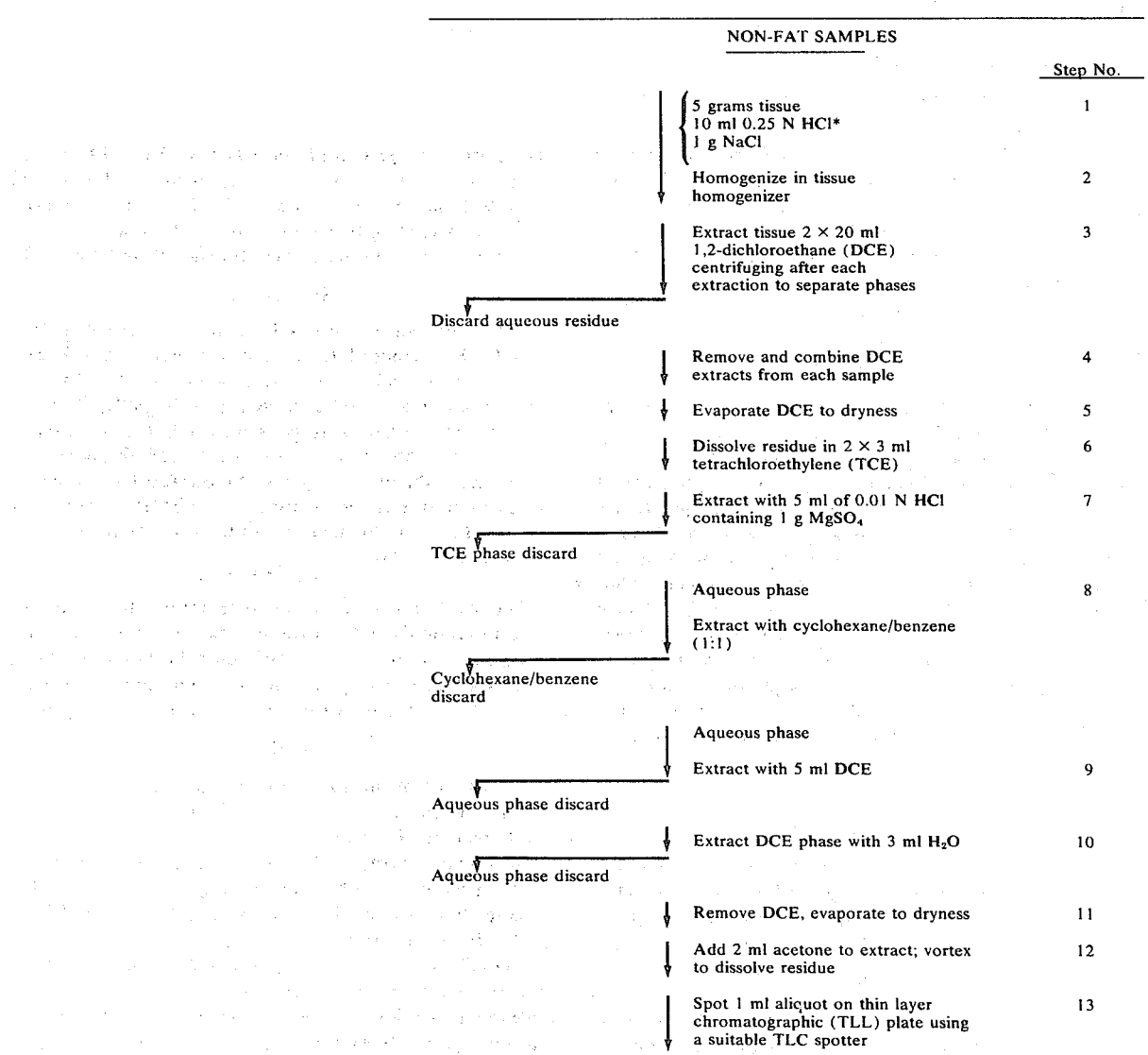

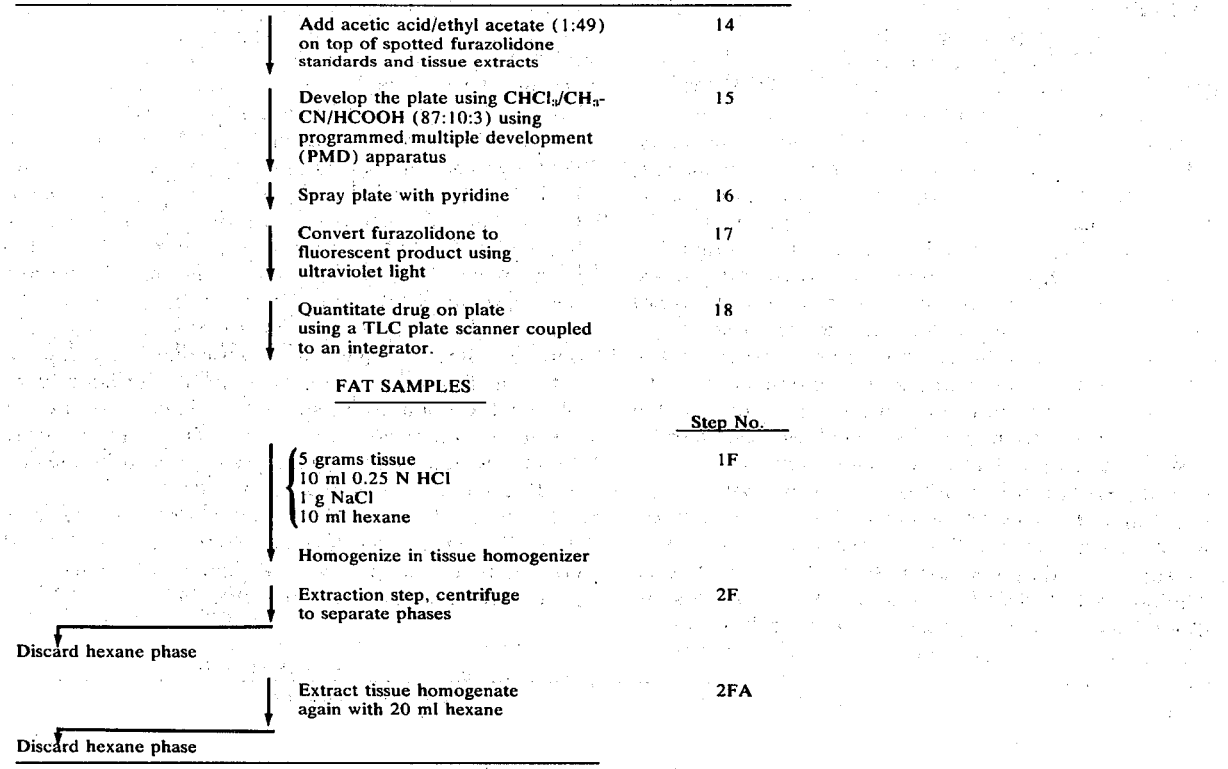

The procedure for "FAT SAMPLES" follows that for "NON-FAT SAMPLES" commencing at Step No. 3.

Step No. 1

Acid must be added to the homogenization medium to adjust pH to <4 to ensure extraction of the drug from the tissue constituents by means of an aqueous-organic extraction procedure.

Step No. 2

A suitable tissue homogenizer is the Polytron homogenizer (Brinkmann Instruments, model PT10 20 3500; Westbury, New York) equipped with the PT10-ST generator. Because of the probe generator structure, a sample can be directly homogenized in the centrifuge tube avoiding loss of the sample in transferring from a blendor cup to a centrifuge tube for extraction. Small volumes (no transfer rinse is needed) may be maintained using this type of homogenizer. Other tissue homogenizers eqivalent to the Polytron homogenizer would be models such as Virtis which homogenize small tissue samples in a small volume of medium but would require transfer of the homogenate from the blendor cup to a centrifuge tube with minimal acid rinse.

Step No. 1F

The addition of hexane to the homogenizing medium aids in the homogenization of fatty tissue. Subsequent removal of lipid tissue constituents is also accomplished, following extraction, centrifugation, phase separation and discard of the hexane phase.

Step No. 3

1,2-Dichloroethane (DCE) is an excellent organic extractant of furazolidone from an aqueous medium. The partition coefficient approaches 14 in a DCE/0.25 N HCl system (no tissue present). Some binding of the drug to tissue occurs. About 80% of the drug is recovered by extracting twice with DCE. Ethyl acetate, acetonitrile or nitromethane may be substituted for DCE.

Step No. 6

Tetrachloroethylene (TCE) is used to dissolve drug and DCE extracted tissue constituents in the round bottom flask. When drug and tissue constituents are partitioned against 0.01 N HCl, plus $MgSO_4$, approximately 98% of the drug goes into the aqueous phase, with most of the tissue constituents remaining in the TCE phase, giving an excellent clean-up step. Carbon tetrachloride may be substituted for TCE. A buffer of pH4 or less may be substituted for 0.01 N HCl.

Step No. 8

The cyclohexane/benzene extraction step removes additional lipids and fluorescent material present in the aqueous extract (0.01 N HCl plus $MgSO_4$). At least 80% of the drug stays in the aqueous phase following extraction, centrifugation, and separation of phases.

Step No. 13

An aliquot of the tissue extract is quantitatively and rapidly transferred (spotted) to the silica gel thin layer plate using a Chromaflex (Kontes Company, Vineland, New Jersey) spotter. Multiple handling and repetitive spotting is minimized, insuring a quantitative transfer of drug from the conical tube to the TLC plate.

Other TLC spotters may be substituted for the Chromaflex spotter as long as the spot diameter does not exceed 1 cm. Repetitive aliquots could be added until an equivalent of one-half the sample was spotted on the TLC plate. Manual repetitive spotting could also be accomplished by adding 5 μl Microcap^R applications, followed by suitable rinses of the vessel containing the sample.

Step No. 14

Handling and light converts a portion of furazolidone, which is the anti isomer, to its syn isomer. A 1:49 ratio of acetic acid/ethyl acetate solution is spotted manually on the furazolidone plate standards and tissue residue extracts converting any furazolidone in the syn isomer to the anti isomer of the parent compound. The conversion of the syn isomer to the anti isomer allows the drug to be chromatographed as a single area instead of a doublet area on the TLC plate.

Ratios other than 1:49 acetic acid/ethyl acetate may be substituted for acetic acid in the mixture.

Step No. 15

Formic acid in the programmed multiple development (PMD, Regis Chemical Company, model 2000 with developer 222, Morton Grove, Illinois) chromatographic solvent insures sharp resolution (bands or lines) of drug separated from tissue constituents. This also keeps the drug in the anti isomer during chromatography.

Programmed multiple development using a suitable solvent system, increases the sensitivity of the assay 10-fold. Using conventional TLC, about 10–15 nanograms of the fluorescent furazolidone product can be quantitated by TLC densitometry, while less than a nanogram of fluorescent furazolidone product can be quantitated using PMD and scanned with a fluorodensitometer coupled with a microvolt integration system.

A manually operated apparatus including sandwich chamber, solvent trough and infrared quartz lamps could be substituted for the PMD apparatus.

Step Nos. 16 & 17

The conversion of furazolidone from an ultraviolet absorbing drug to a fluorescent product permits quantitative measurement of less than a nanogram of drug on a TLC plate. In a two step reaction, spraying the plate with pyridine using a reagent sprayer (Camag Company, New Berlin, Wisconsin) converts furazolidone to a complex which is, in turn, converted to a fluorescent product by irradiation with ultraviolet light. Other TLC sprayers could be used if a fine mist of pyridine was delivered to the plate. Equilibration in a pyridine saturated TLC tank or closed container, with the plate supported above the solvent may also be substituted for the sprayer. A PMD developing solvent containing small volumes of pyridine may also be substituted for the pyridine spray.

Step No. 18

The Farrand VIS-UV Chromatogram Analyzer, (Farrand Optical Company, catalog No. 134180, Valhall, New York) in the fluorescence mode, can detect less than one nanogram of fluorescent furazolidone product. Furazolidone is developed on the TLC plate using the PMD and then converted to the fluorescent product.

The AutoLab System I Integrator (ASI) (Spectra Physics, Auto Lab Division, model 22000–010, Parsippany, New Jersey) is capable of measuring millivolt signals from a TLC scanner with a microvolt computerized integration system. Defined peak areas, based on plate standard retention time (distance from spot origin/scan rate), are automatically converted to nanograms of compound when divided by the plate standard KF factor, determined from calibration scans of the plate standards. Resolved baseline corrections, if needed to integrate peak areas, are automatically made. Integrators with millivolt integration systems would not be acceptable for quantitation of the drug at the nanogram level unless the scan signal was amplified.

Shoeffel, Zeiss, Aminco-Bowman and the other TLC plate scanners in the fluorescence mode may be used as long as their monochromators, optics and signal output are comparable to the Farrand VIS-UV Chromatogram Analyzer.

The AutoLab System 4 Integrator (Spectra Physics) may be substituted as well as other integrators which can handle a 1 millivolt densitometric signal output, resolve peak baselines, and integrate peaks using a computerized microvolt signal. A millivolt integrator may be substituted if the scanner signal is amplified.

The method of the instant invention permits determination of furazolidone in animal tissue on samples of 10 grams or less; shortens the time of single sample assay to about 4 hours; increases sensitivity to nanogram and picogram levels; and direct measurement of a fluorescent product in comparison with a standard sample.

What is claimed is:

1. A method for the determination of furazolidone in edible animal tissue comprising spotting a TLC plate with a solution containing furazolidone extracted from said tissue, developing the TLC plate, contacting the developed TLC plate with pyridine, exposing the contacted TLC plate to ultraviolet light, and relating the resulting fluorescence to the furazolidone determination.

* * * * *

PO-1050
(5/69)

UNITED STATES PATENT OFFICE
CERTIFICATE OF CORRECTION

Patent No. 3,980,434  Dated September 14, 1976

Inventor(s) James L. Mertz, Joanne Olivard and James P. Heotis

It is certified that error appears in the above-identified patent and that said Letters Patent are hereby corrected as shown below:

On the title page, [75] Inventors: should read

[75] Inventors: James L. Mertz, Norwich, N.Y.; Joanne Olivard, Honey Groves, Texas; James P. Heotis, Norwich, N.Y.

Signed and Sealed this

Twenty-first Day of December 1976

[SEAL]

Attest:

RUTH C. MASON
*Attesting Officer*

C. MARSHALL DANN
*Commissioner of Patents and Trademarks*